United States Patent [19]

Warrin

[11] Patent Number: 4,682,949
[45] Date of Patent: Jul. 28, 1987

[54] TOOL HOLDER FOR ULTRASONIC ENDODONTIC APPARATUS

[75] Inventor: George E. Warrin, North Merrick, N.Y.

[73] Assignee: Dentsply Research & Development Corp., Milford, Del.

[21] Appl. No.: 754,175

[22] Filed: Jul. 12, 1985

[51] Int. Cl.⁴ .............................................. A61C 5/02
[52] U.S. Cl. ...................................... 433/81; 433/127
[58] Field of Search ............... 433/102, 127, 128, 129, 433/81; 128/305; 604/22; 279/1 B, 1 TE, 77, 78, 76

[56]  References Cited

U.S. PATENT DOCUMENTS

| | | | |
|---|---|---|---|
| 2,360,907 | 10/1944 | Stoner | 279/1 TE |
| 2,442,033 | 5/1948 | Brantley et al. | 32/28 |
| 2,816,770 | 12/1957 | DeVlieg et al. | 279/77 |
| 2,853,781 | 9/1958 | Hoffmeister | 433/127 |
| 3,108,781 | 10/1963 | Saffir | 253/3 |
| 3,219,356 | 11/1965 | Wilterdink et al. | 279/1 B |
| 3,451,134 | 6/1969 | Erickson et al. | 32/28 |
| 3,952,416 | 4/1976 | Lingenhole | 32/27 |
| 4,492,572 | 1/1985 | Warrin et al. | 433/81 |
| 4,492,574 | 1/1985 | Warrin et al. | 433/81 |
| 4,505,676 | 3/1985 | Gonser | 433/127 |

Primary Examiner—Robert Peshock
Attorney, Agent, or Firm—Vorys, Sater, Seymour & Pease

[57]  ABSTRACT

A tool holder preferably for an ultrasonic endodontic apparatus includes an eccentric member in the holder to secure the butt end of a tool thereon by a camming action during limited rotation of a cam member. The tool holder also includes an irrigating fluid passage located proximate to, but remote from, a tool-receiving bore in the tool holder to direct irrigating fluid onto the tool. An eccentric cam is mounted in a cross-bore within the tool holder, located relative to a tool-receiving bore having a predetermined longitudinal depth, so that a camming action of the eccentric cam longitudinally seats the tool deep in the bore while securing it there by the cam upon limited rotational motion of the cam. The cam includes tool pads for receiving mating surfaces of a bifurcated wrench.

28 Claims, 5 Drawing Figures

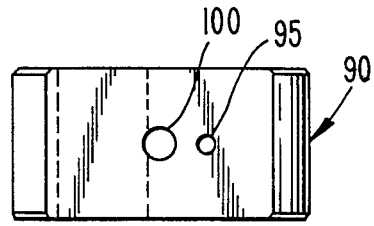
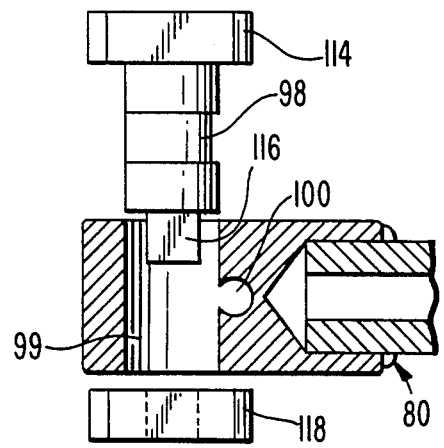
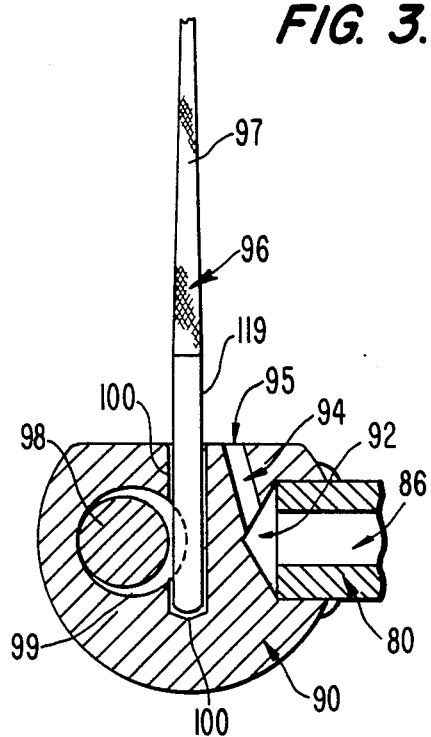
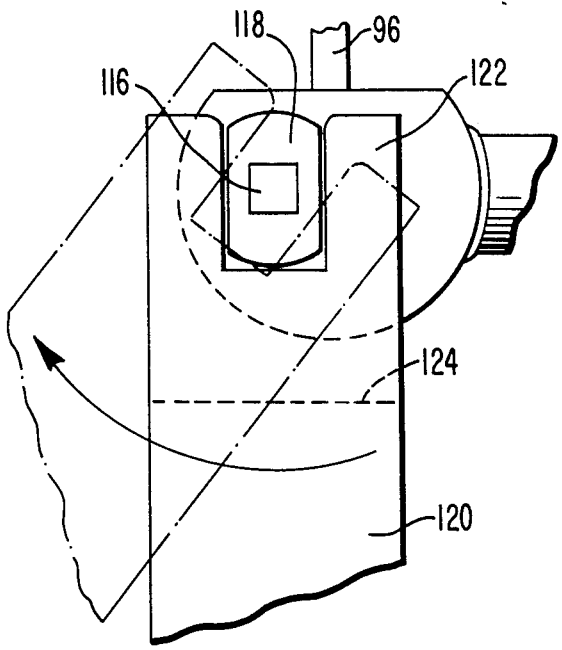

TOOL HOLDER FOR ULTRASONIC ENDODONTIC APPARATUS

BACKGROUND OF THE INVENTION

1. Field of the Invention

This invention relates to ultrasonic endodontic dental apparatus, and more particularly to an improved endodontic tool holder and root canal irrigating apparatus adapted to be used with an ultrasonic dental handpiece for debriding root canals and for directing fluid solutions, including medicaments, along the endodontic instrument for irrigating and treating the root canal during use of the instrument. Still more particularly, the invention relates to a tool holder having means for readily exchanging tool members by pivoting an eccentric member in the holder to secure the tool member, the tool holder also preferably including a fluid irrigating passage therein for irrigating the tool member.

2. Description of the Prior Art

Ultrasonic endodontic dental appliances employed for cutting or cleaning in dental procedures are known in which a liquid, conventionally water, flows through the handpiece to cool the handpiece. Such cooling water also flows through the ultrasonically driven tool mounting head and is discharged from the head in the direction of the tool tip to irrigate and cool the work area. One such device is disclosed, for example, in U.S. Pat. No. 4,492,574 and the present invention is particularly well adapted for use in ultrasonic devices of the type disclosed in this prior patent, the disclosure of which is incorporated herein by reference and reference to which may be had for a more complete understanding of the construction and operation of such appliances.

Endodontic files used in the performance of root canal therapy are supported for axial or longitudinal ultrasonic vibration in the head and can be ultrasonically vibrated in a transverse, wave-like motion to enhance the debriding action. It is known to provide an irrigating fluid directed along an ultrasonically vibrating endodontic file longitudinally of the axis of the file to provide irrigation of the root canal while the debriding action is proceeding; however, in the known apparatus at least part of the shaft of a file that is inserted in the head is not supported by the head. Instead of supporting the entire length of the shaft that is inserted in the head, a gap is provided between the shaft and the head, near the surface of the head, as a channel for the irrigation fluid. In this known apparatus, the butt end of the shaft is clamped in the head by a set screw, which contacts a longitudinal surface of the shaft to eliminate the instability that could occur in such apparatus if the shaft of the file were only clamped at a given point. However, the file may rock if the butt of the shaft is not fully inserted in the head. Because of the tiny size of the files, the critical distance between full insertion and an insecure position is very small, and the files themselves are difficult to manipulate. Securing such files in the known apparatus is thus somewhat difficult and so a risk that the file will be inadequately supported, or will even work loose, is present. Furthermore, the proper installation of endodontic files in such apparatus is both awkward and time-consuming.

SUMMARY OF THE INVENTION

An object of the invention is to provide improved ultrasonic endodontic apparatus, whereby an endodontic file is securely supported in the tool support assembly and a flow of irrigating fluid is provided to the abrasive surface of the file.

Another object of the invention is to provide a tool holder to enable endodontic files to be quickly and easily affixed to the tool support assembly.

Another object of the invention is to provide a clamping structure in a tool holder to assure that endodontic files are fully inserted in the tool support assembly.

A more general object of the invention is to provide a tool holder capable of securing at least a portion of an elongated tool therein by a clamping device having an eccentric member, so that limited rotation of the eccentric member secures the portion of the elongated tool.

In connection with the foregoing more general object, it is another general object of the invention to provide a liquid flow hole in the tool holder located to direct irrigating fluid to the elongated tool, or toward the working surface of the tool.

In the attainment of the foregoing and other objects and advantages, an important feature of the present invention resides in providing an eccentric cam which is adapted to move the shaft of the file in the head of the tool support assembly so that rotation of the cam in a given direction will move the shaft into the head as the cam clamps the shaft of the file in the head.

In accordance with the present invention, the length of the shaft that is inserted in the head is supported by the head and a flow of irrigation fluid is provided through an orifice in the head that is proximate to, but remote from, the bore in which the shaft of the file is inserted. The flow of irrigation fluid from the orifice is directed at an oblique angle to the file onto the abrasive surface of the file.

BRIEF DESCRIPTION OF THE DRAWINGS

These and other objects and advantages of the invention will be more readily understood when the detailed description appearing hereinbelow is considered in conjunction with the drawings provided, in which:

FIG. 2 is a schematic view of the underside of the tool mounting head of the ultrasonic endodontic apparatus shown in FIG. 1;

FIG. 3 is a detailed view of the tool mounting head of the apparatus shown in FIG. 1;

FIG. 4 is an exploded end view of the tool mounting head shown in FIG. 3; and

FIG. 5 is a schematic diagram of a wrench used with the tool mounting head shown in FIG. 4.

DETAILED DESCRIPTION OF A PREFERRED EMBODIMENT

Figure 1:
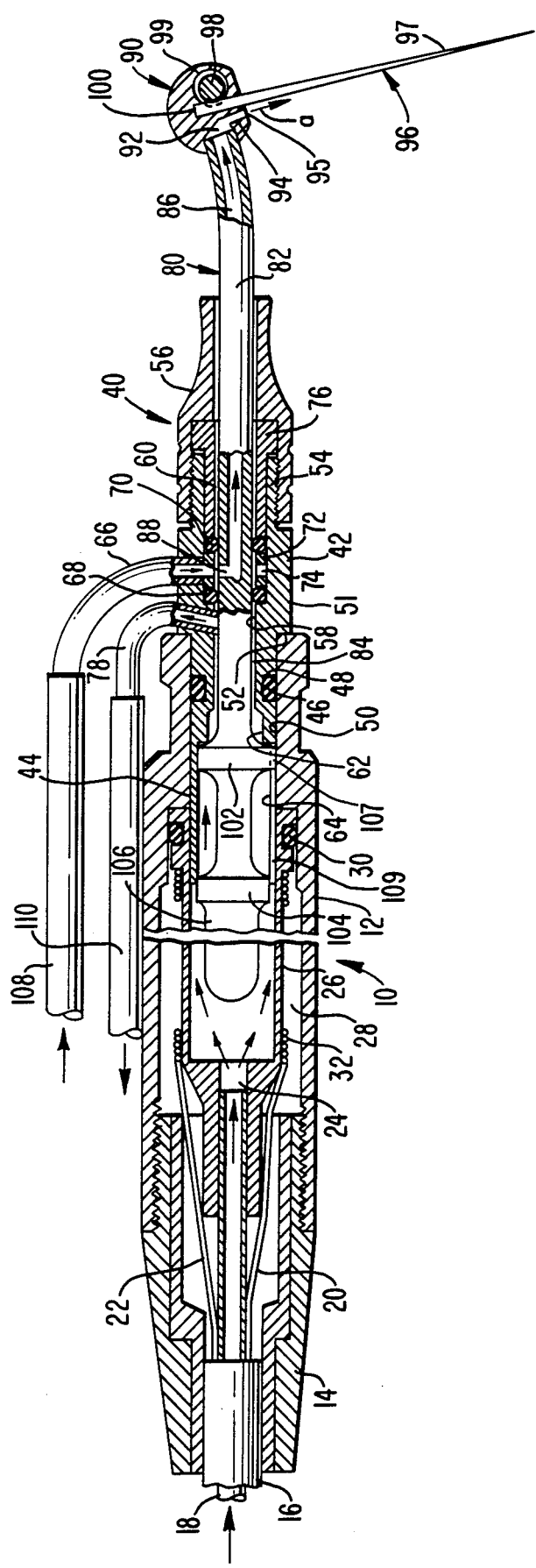
FIG. 1 is a longitudinal sectional view of an ultrasonic device having an insert assembly with a tool mounting head constructed in accordance with the preferred embodiment of the present invention.

Ultrasonic cleaning instruments are well-known and widely used in the dental art and numerous commercial devices are available which accomplish various procedures and are particularly adapted to satisfy the preferences of the individual operator. The present invention is particularly well adapted for, but not limited to use with an ultrasonic dental cleaning device of the type disclosed and described in the above-mentioned patent which incorporates means for flowing a liquid through the handpiece to cool the electrically-excited ultrasonic device.

While operation of the ultrasonic device is described in detail in the aforementioned patent, the basic structure will be briefly described here to facilitate understanding of the present invention. Also, while the entire assembly illustrated in FIG. 1 is sometimes referred to generally as a "handpiece", this term is used herein to refer only to the rigid housing and electrical components at the aft section of the instrument whereas the removable portion at the forward or working end of the apparatus will be referred to as an "insert assembly". Thus, except for the tool holder which is the subject of this invention, FIG. 1 of this application is quite like FIG. 1 of U.S. Pat. No. 4,492,574.

The ultrasonic handpiece is indicated generally in FIG. 1 by the reference numeral 10 and includes an outer, substantially cylindrical tubular housing 12 closed at its aft end by a threaded end cap member 14. A compound cable assembly 16 is mounted in and extends through the end cap 14 and contains a central flexible hose 18 and a pair of electrical conductors or wires 20, 22.

The flexible hose 18 extends into and forms a fluid-tight seal with an axial opening 24 in the end of an internal housing member 26 which is mounted coaxially within and in an inwardly spaced relation to the inner surface of the housing 12 to define an annular space 28. An O-ring seal 30 on the forward end of the inner housing 26 cooperates with the inner surface of the outer housing 12 to form a fluid-tight seal adjacent the forward end of the handpiece. Conductors 20, 22 are connnected to the windings of a coil, indicated generally at 32, wound on the outer surface of the inner housing 26 so that, when the conductors 20, 22 are connected to a suitable power source externally of the handpiece, a high frequency alternating electromagnetic field is established. The forward end of the outer housing 12 has a reduced diameter bore corresponding to the internal diameter of the inner housing 26, with the two surfaces being adapted to telescopingly receive and support a cylindrical surface on a separable, cooperating insert assembly 40. The insert assembly 40 is retained by friction to enable easy separation and replacement with another insert assembly.

Referring to the forward, or operative end of the apparatus, i.e., the end at the right in FIG. 1, the removable dispensing insert assembly 40 comprises an elongated rigid body member 42 including a central section 44 with a cylindrical outer surface substantially equal to the diameter of the inner surface of the inner housing member 26 and the forward end of the outer housing member 12. An O-ring seal 46 mounted within an O-ring groove 48 frictionally engages the inner surface 50 of the housing 12 to provide a fluid-tight seal between body 42 and the outer housing 12 and to resiliently retain the body within the housing. The forward portion 51 of the body 42 is of enlarged diameter and provides a shoulder 52 adapted to engage the forward end of the outer housing 12 to accurately position the insert within the handpiece. The forward section 54 of the body 42 is threaded on its outer surface to threadably engage and support an internally threaded nut member 56. A small diameter bore 58 extends axially through the body 42, and a counterbore 60 extends into the body member from its forward end to a position within the enlarged forward section 51. Also, first and second counterbores formed in the rear end of the body 42 provide first and second cylindrical surfaces 62, 64.

A rigid tubular elbow member 66 has one end mounted in a radial bore in the enlarged central section 51 of the body 42, with the tubular member preferably being secured by brazing or welding to provide a rigid watertight seal. A pair of O-rings 68, 70 mounted within the counterbore 60 retain an annular spacer sleeve 72, and radially extending openings 74 formed in the spacer sleeve permit the flow of liquid from the tubular member 66 through the spacer member. A retaining sleeve 76 is telescopingly received in the forward end of body 42 to position the O-rings 68, 70 and spacer sleeve 72, with the sleeve 76 being held in position by the threaded nut 56.

A second rigid curved tubular member 78 is secured, as by brazing, in a second generally radially extending bore in the enlarged section of the body 42 and provides fluid communication with the small diameter bore section 58 at a location rearward from the O-ring seal 68. The function of this second tubular member will be described more fully hereinbelow.

An elongated tool support assembly 80 is slidably supported within body member 42 and includes a rigid shank portion 82 having an external diameter slightly less than the diameter of the bore 58 to provide an annular fluid flow passage 84 therebetween. An axial bore 86 is formed in the outwardly projecting end of the shank 82, with the bore 86 terminating at a location between the O-rings 68 and 70. A radial bore 88 provides a fluid flow path from the tubular member 66 and the openings 74 in the spacer member 72 into the bore 86.

A body of magnetostrictive material is rigidly mounted, as by brazing or welding, on the aft end of the connecting body portion of the tool support assembly and is excited in the longitudinal direction by the high frequency field established by the coil 32 to impart the desired longitudinal vibrations to the tool support assembly. These vibrations are transmitted in the conventional manner through the rigid metal of the shank 82 and imparted to the root canal file in a direction substantially transversely of its longitudinal axis to establish a standing wave-like vibration pattern to the file which is highly effective in debriding a root canal.

The improvement according to the invention here disclosed relates to an improved tool holder 90 which is constructed to include means for readily securing a portion of a tool therein by limited rotation of an eccentric member. The rotation of the eccentric, as will be more fully described, securely clamps the tool (preferably a file) in place while securely positioning the tool at the bottom of the opening for receiving the tool. Another significant feature of the improved tool holder is found in its inclusion of an angled fluid opening, positioned near but remote from the tool, and angled to provide irrigating fluid to be directed to the tool, or preferably to the working surface on the tool. The position of the angled fluid opening in the tool holder permits the tool to be clamped in line with the eccentric clamping action.

The enlarged head member 90, acting as a tool holder, is rigidly mounted, as by brazing or welding, on the distal end of the shank 82 and a bore 92 extends through the head to communicate with the axial bore 86 in shank 82. An angled bore 94 is formed in the head 90, and extends transversely of the bore 92 to open from the head member 90 through an orifice 95 proximate to the butt end of the replaceable root canal file 96. The angled bore 94 directs irrigating fluid from the axial bore 86 against the file 96 so that the irrigating fluid flows onto the abrasive working surface 97, as shown by the arrow a in FIG. 1. The spatial relationship between the orifice 95 and a tool mounting bore 100 on the underside of the head 90 is more clearly seen in FIG. 2.

As shown in FIG. 3, the head 90 includes an eccentric cam 98 mounted in a crossbore 99 in the tool mounting head 90. Typically, the head generally has the shape of a truncated cylinder. The cam 98 is structurally adapted to engage and firmly retain the butt end of the root canal file 96 when seated in the head 90. The camming surface is shaped so that, as the cam 98 is rotated, the file 96 is moved longitudinally in the mounting bore 100. The diameter of the mounting bore 100 in which the butt end of the shaft of the file 96 is inserted is very similar to the diameter of the butt of the file, so that the entire length of that portion of the file 96 that is inserted into the tool mounting head is supported by the tool mounting head 90.

A tool support assembly, designated generally by the reference numeral 80, has a connecting body portion disposed within the aft end of the body 42, with the connecting body including a pair of enlarged sections 102, 104 each having a diameter slightly less than the diameter of the cylindrical surface 64. A key 107 integrally formed on the cylindrical connecting body portion 102 is disposed with an elongated slot 109 in the wall of the body member 42 to prevent rotation of the tool support assembly within the body member.

Irrigation fluid under pressure is admitted through the flexible tube 108 and flows through the connecting tube 66 into the bore 60 of the body member 42 and, being restricted by the O-rings 68 and 70, is confined to flow through the radial bore 88 and the axial bore 86 to the vibrating head 90 to be discharged through the orifice 95 proximate to the root canal file 96.

Cooling water admitted to the handpiece through flexible tube 18 is permitted to flow through the handpiece within the inner housing 26 and over the surface of the magnetostrictive material 106 and connecting body portions 102, 104 to the annular space 84. The O-ring 68 blocks flow of the cooling fluid beyond this point, forcing it to flow out through the outlet tube 78. A flexible tube 110 is connected to the outlet tubular member 78 to provide an escape for the cooling fluid which would normally be from the orifice 95 in the tool mounting head on the insert assembly when the handpiece is used in connection with a cleaning tool or the like. Thus, apparatus in accordance with the preferred embodiment provides a flow of cooling fluid through the handpiece while at the same time providing a flow path for an irrigation fluid which flow path is completely isolated from the cooling fluid.

With regard to FIG. 4, the eccentric cam 98 of the presently preferred embodiment is formed with an integral flange 114 on one end and a spline 116 on the other end. The cam 98 is snugly fitted into the crossbore 99 and the retaining flange 118 is then fitted onto the spline 116 and permanently staked to it. The shaft 119 of the file 96 is then inserted into the head 90 with the eccentric cam 98 rotated so that the smallest radius of the cam 98 is toward the mounting bore 100.

The wrench 120, shown in FIG. 5, which includes a bifurcated end, is then applied to the flanges 114, 118, of the eccentric cam 98 to clamp the shaft of the file 96 in the head 90 by rotating the cam in a clock-wise direction, as viewed from the side on which the retaining flange 118 is mounted. As the cam 98 rotates, the shaft 119 is forced further into the mounting bore 100. The cam is rotated in a clockwise direction until resistance to further rotation indicates that the shaft 119 is tightly clamped in the mounting bore 100 by a surface of the eccentric cam somewhere between the maximum and minimum radii of the cam 98. The center of the wrench 120, between the prongs 122 that engage the flanges 114, 118, is cutaway. This cutaway, indicated in phantom at 124, is located at a distance greater than the outermost extent of the head 90 for the axis of rotation of the cam, and permits the wrench to rotate freely through an arc of more than 180° about the head 90 when applied to the head 90 to rotate the flanges 114, 118. Rotating both flanges 114, 118, simultaneously distributes the load on the cam 98, thereby providing more efficient clamping and reducing wear on the cam 98. Thus the tool is securely and effectively seated on the bore by the camming action of the tool holder.

It should be apparent that various modifications may be made to the embodiment described above. For example, the tool support assembly might be affixed to the handpiece, or the irrigation and cooling fluid paths might be the same path. Accordingly, while a preferred embodiment of the invention has been disclosed and described, it should be understood that it is not intended to be so limited but rather it is intended to include all embodiments which would be apparent to one skilled in the art and which come within the spirit and scope of the invention.

I claim:

1. An ultrasonic endodontic apparatus for use with an endodontic tool having a mounting shaft and a working surface comprising:
    an ultrasonic dental handpiece adapted to deliver vibratory energy and a flow of irrigation fluid,
    a tool support assembly adapted to be connected to said handpiece and having a tool mounting head adapted to receive said vibratory energy and said flow of irrigation fluid from said handpiece,
    said head including a tool mounting bore therein adapted to receive the mounting shaft of the endodontic tool,
    an eccentric cam positioned generally in said head for tightly clamping the mounting shaft of the endodontic tool in said head,
    said eccentric cam being adapted to move the mounting shaft in said tool mounting bore so that the mounting shaft is inserted further into said tool mounting bore as said eccentric cam is tightened in a given direction,
    said eccentric cam terminating in a flange at each end thereof,
    said flanges being adapted to rotate said eccentric cam to thereby clamp the tool in said head, and
    a wrench adapted to engage both of said flanges and to pivot about said head while engaged therewith to thereby clamp the tool in said head.

2. The apparatus of claim 1 including,
    said head including a fluid orifice therethrough, proximate to, but spaced from, said tool mounting bore for directing said flow of irrigation at an oblique angle to the longitudinal axis of the tool and onto the working surface of the tool when the tool is mounted in said tool mounting bore.

3. The apparatus of claim 2 including,
    said head including a generally planar face, and said tool mounting bore and said fluid orifice engaging said face.

4. The apparatus of claim 1 including, said eccentric cam engaging an elongated straight surface of the mounting shaft.

5. The apparatus of claim 1 including,
said tool mounting bore including a bore bottom surface, and
said eccentric cam, when tightened in said given direction, positioning the tool shaft generally against said bore bottom surface.

6. The apparatus of claim 1 including,
said eccentric cam including a cylindrical tool engaging portion having a central longitudinal axis and a mounting means for mounting said cylindrical tool engaging portion so it is rotatable within said head about a rotation axis offset from said central longitudinal axis.

7. The apparatus of claim 1 including,
said tool support assembly being affixed to said handpiece.

8. An ultrasonic endodontic apparatus for use with an endodontic tool having a mounting shaft and a working surface comprising:
an ultrasonic dental handpiece adapted to deliver vibratory energy and a flow of irrigation fluid,
a tool support assembly adapted to be connected to said handpiece and having a tool mounting head adapted to receive said vibratory energy and said flow of irrigation fluid from said handpiece,
said head including a tool mounting bore therein adapted to receive the mounting shaft of the endodontic tool,
an eccentric cam positioned generally in said head for tightly clamping the mounting shaft of the endodontic tool in said head,
said eccentric cam being adapted to move the mounting shaft in said tool mounting bore so that the mounting shaft is inserted further into said tool mounting bore as said eccentric cam is tightened in a given direction,
said eccentric cam being positioned in said cross-bore to exhibit a surface free from contact with the tool at a first rotating position of said eccentric cam and a surface in contact with the tool at a different second rotating position of said eccentric cam,
said eccentric cam including a torque-receiving surface for providing rotation thereto, whereupon during rotation of said eccentric cam from said first rotating position to said second rotating position, the tool is longitudinally located at an extent of said tool-mounting bore in said head and secured therein by contact with said eccentric cam,
said torque-receiving surface including a pair of remotely-spaced tool pads at distal ends of said eccentric cam and located outside of the peripheral extent of said head, and
said torque receiving surfaces being structurally adapted for receiving mating surfaces of a bifurcated tool.

9. The apparatus of claim 8 including,
said head including a fluid orifice therethrough, proximate to, but spaced from, said tool mounting bore for directing said flow of irrigation fluid at an oblique angle to the longitudinal axis of the tool and onto the working surface of the tool when the tool is mounted in said tool mounting bore.

10. The apparatus of claim 9 including, said head including a generally planar face, and said tool mounting bore and said fluid orifice engaging said face.

11. The apparatus of claim 8 including,
said eccentric cam engaging an elongated straight surface of the mounting shaft.

12. The apparatus of claim 8 including,
said tool mounting bore including a bore bottom surface, and
said eccentric cam, when tightened in said given direction, positioning the tool shaft generally against said bore bottom surface.

13. The apparatus of claim 8 including,
said eccentric cam including a cylindrical tool engaging portion having a central longitudinal axis and a mounting means for mounting said cylindrical tool engaging portion so it is rotatable within said head about a rotation axis offset from said central longitudinal axis.

14. The apparatus of claim 8 including,
said tool support assembly being affixed to said handpiece.

15. An ultrasonic endodontic apparatus for use with an endodontic tool having a mounting shaft and a working surface comprising:
an ultrasonic dental handpiece adapted to deliver vibratory energy and a flow of irrigation fluid,
a tool support assembly adapted to be connected to said handpiece and having a tool mounting head adapted to receive said vibratory energy and said flow of irrigation fluid from said handpiece,
said head including a tool mounting bore therein adapted to receive the mounting shaft of the endodontic tool,
an eccentric cam positioned generally in said head for tightly clamping the mounting shaft of the endodontic tool in said head,
said eccentric cam being adapted to move the mounting shaft in said tool mounting bore so that the mounting shaft is inserted further into said tool mounting bore as said eccentric cam is tightened in a given direction, and
said eccentric cam including an integral flange at a first end thereof, a spline at a second end thereof, and a retaining flange which is fitted on and secured to said spline, after said second end has been fitted in said head.

16. The apparatus of claim 15 including,
said head including a fluid orifice therethrough, proximate to, but spaced from, said tool mounting bore for directing said flow of irrigation fluid at an oblique angle to the longitudinal axis of the tool and onto the working surface of the tool when the tool is mounted in said tool mounting bore.

17. The apparatus of claim 16 including, said head including a generally planar face and said tool mounting bore and said fluid orifice engaging said face.

18. The apparatus of claim 15 including, said eccentric cam engaging an elongated straight surface of the mounting shaft.

19. The apparatus of claim 15 including, said tool mounting bore including a bore bottom surface, and
said eccentric cam, when tightened in said given direction, positioning the tool shaft generally against said bore bottom surface.

20. The apparatus of claim 15 including,
said eccentric cam including a cylindrical tool engaging portion having a central longitudinal axis and a mounting means for mounting said cylindrical tool engaging portion so it is rotatable within said head about a rotation axis offset from said central longitudinal axis.

21. The apparatus of claim 15 including,
said tool support assembly being affixed to said handpiece.

22. An ultrasonic endodontic apparatus for use with an endodontic tool having a mounting shaft and a working surface comprising:
an ultrasonic dental handpiece adapted to deliver vibratory energy and a flow of irrigation fluid,
a tool support assembly adapted to be connected to said handpiece and having a tool mounting head adapted to receive said vibratory energy and said flow of irrigation fluid from said handpiece,
said head including a tool mounting bore therein adapted to receive the mounting shaft of the endodontic tool,
an eccentric cam positioned generally in said head for tightly clamping the mounting shaft of the endodontic tool in said head,
said eccentric cam being adapted to move the mounting shaft in said tool mounting bore so that the mounting shaft is inserted further into said tool mounting bore as said eccentric cam is tightened in a given direction,
said eccentric cam including a rotating cam surface which directly engages the mounting shaft of the tool for moving the tool further into said tool mounting bore,
said eccentric cam including a first end and a first grasping means at said first end adapted to be grasped and turned to move the tool into said tool mounting bore,
said eccentric cam including a second end opposite to said first end and a second grasping means at said second end adapted to be grasped and turned to move the tool into said tool mounting bore, and
a bifurcated wrench adapted to simultaneously engage and turn said first and second grasping means.

23. The apparatus of claim 22 including,
said head including a fluid orifice therethrough, proximate to, but spaced from, said tool mounting bore for directing said flow of irrigation fluid at an oblique angle to the longitudinal axis of the tool and onto the working surface of the tool when the tool is mounted in said tool mounting bore.

24. The apparatus of claim 23 including,
said head including a generally planar face and said tool mounting bore and said fluid orifice engaging said face.

25. The apparatus of claim 22 including,
said eccentric cam engaging an elongated straight surface of the mounting shaft.

26. The apparatus of claim 22 including,
said tool mounting bore including a bore bottom surface, and
said eccentric cam, when tightened in said given direction, positioning the tool shaft generally against said bore bottom surface.

27. The apparatus of claim 22 including,
said eccentric cam including a cylindrical tool engaging portion having a central longitudinal axis and a mounting means for mounting said cylindrical tool engaging portion so it is rotatable within said head about a rotation axis offset from said central longitudinal axis.

28. The apparatus of claim 22 including, said tool support assembly being affixed to said handpiece.

* * * * *